United States Patent
Wingardner et al.

(10) Patent No.: US 9,265,585 B2
(45) Date of Patent: Feb. 23, 2016

(54) SURGICAL INSTRUMENT WITH RAPID POST EVENT DETECTION

(71) Applicant: Covidien LP, Mansfield, MA (US)

(72) Inventors: Thomas Wingardner, North Haven, CT (US); Philip Irka, Northford, CT (US); Michael Ingmanson, Stratford, CT (US)

(73) Assignee: Covidien LP, Mansfield, MA (US)

( * ) Notice: Subject to any disclaimer, the term of this patent is extended or adjusted under 35 U.S.C. 154(b) by 651 days.

(21) Appl. No.: 13/658,219

(22) Filed: Oct. 23, 2012

(65) Prior Publication Data

US 2014/0110453 A1    Apr. 24, 2014

(51) Int. Cl.
*A61B 17/068* (2006.01)
*A61B 19/00* (2006.01)
*A61B 17/072* (2006.01)
*A61B 17/00* (2006.01)

(52) U.S. Cl.
CPC ............ *A61B 19/30* (2013.01); *A61B 17/07207* (2013.01); *A61B 2017/00017* (2013.01); *A61B 2017/00398* (2013.01); *A61B 2017/00464* (2013.01); *A61B 2017/00473* (2013.01); *A61B 2017/00734* (2013.01); *A61B 2019/4847* (2013.01); *A61B 2019/4863* (2013.01); *A61B 2019/4873* (2013.01)

(58) Field of Classification Search
CPC ..................... A61B 17/00; A61B 2017/00017; A61B 17/068
USPC ....................................................... 227/175.2
See application file for complete search history.

(56) References Cited

U.S. PATENT DOCUMENTS

| | | |
|---|---|---|
| 5,433,721 A | 7/1995 | Hooven et al. |
| 5,469,215 A | 11/1995 | Nashiki |
| 5,518,163 A | 5/1996 | Hooven |
| 5,543,695 A | 8/1996 | Culp et al. |
| 5,563,481 A | 10/1996 | Krause |
| 5,602,449 A | 2/1997 | Krause et al. |
| 5,747,953 A | 5/1998 | Philipp |
| 5,804,936 A | 9/1998 | Brodsky et al. |
| 5,928,256 A | 7/1999 | Riza |
| 6,013,991 A | 1/2000 | Philipp |
| 6,017,354 A | 1/2000 | Culp et al. |
| 6,025,683 A | 2/2000 | Philipp |
| 6,090,123 A | 7/2000 | Culp et al. |

(Continued)

FOREIGN PATENT DOCUMENTS

| | | |
|---|---|---|
| EP | 1 240 709 B1 | 11/2005 |
| EP | 1759652 A2 | 3/2007 |

OTHER PUBLICATIONS

European Search Report No. 13189650.8 dated Sep. 10, 2014.

*Primary Examiner* — Gloria R Weeks

(57) ABSTRACT

A surgical instrument is disclosed, the instrument including: a handle assembly; a jaw assembly including a staple cartridge containing a plurality of staples and an anvil to form the plurality of staples upon firing; a lockout mechanism configured to prevent reuse of the jaw assembly; a drive assembly at least partially located within the handle and connected to the jaw assembly; a motor operatively coupled to the drive assembly; and a controller operatively coupled to the motor, the controller configured to control supply of electrical current to the motor and to monitor a current draw of the motor, wherein the controller is further configured to terminate the supply of electrical current to the motor in response to a drop in the current draw.

18 Claims, 14 Drawing Sheets

(56) References Cited

U.S. PATENT DOCUMENTS

| | | |
|---|---|---|
| 6,329,778 B1 | 12/2001 | Culp et al. |
| 6,377,008 B1 | 4/2002 | Hirata |
| RE38,486 E | 4/2004 | Sakabe |
| 7,362,062 B2 | 4/2008 | Schneider et al. |
| 7,400,107 B2 | 7/2008 | Schneider et al. |
| 7,432,677 B2 | 10/2008 | Heydt et al. |
| 7,514,890 B2 | 4/2009 | Schneider et al. |
| 7,721,931 B2 | 5/2010 | Shelton, IV et al. |
| 7,721,936 B2 * | 5/2010 | Shalton et al. ............ 227/180.1 |
| 7,738,971 B2 | 6/2010 | Swayze et al. |
| 7,755,310 B2 | 7/2010 | West et al. |
| 7,810,691 B2 | 10/2010 | Boyden et al. |
| 7,843,158 B2 | 11/2010 | Prisco |
| 7,866,527 B2 | 1/2011 | Hall et al. |
| 7,898,198 B2 | 3/2011 | Murphree |
| 7,905,380 B2 | 3/2011 | Shelton, IV et al. |
| 7,911,168 B2 | 3/2011 | Koike |
| 7,954,682 B2 * | 6/2011 | Giordano et al. .......... 227/175.1 |
| 7,960,931 B2 | 6/2011 | Rodriguez et al. |
| 7,994,746 B2 | 8/2011 | Chiu et al. |
| 7,998,157 B2 | 8/2011 | Culp et al. |
| 8,020,743 B2 | 9/2011 | Shelton, IV |
| 8,028,885 B2 | 10/2011 | Smith et al. |
| 8,038,046 B2 | 10/2011 | Smith et al. |
| 8,154,239 B2 | 4/2012 | Katsuki et al. |
| 8,157,153 B2 | 4/2012 | Shelton, IV et al. |
| 8,161,977 B2 | 4/2012 | Shelton, IV et al. |
| 8,241,322 B2 | 8/2012 | Whitman et al. |
| 8,752,749 B2 | 6/2014 | Moore et al. |
| 2010/0076474 A1 | 3/2010 | Yates et al. |
| 2010/0244757 A1 | 9/2010 | Tsai et al. |
| 2011/0006101 A1 | 1/2011 | Hall et al. |
| 2011/0017801 A1 | 1/2011 | Zemlok et al. |
| 2011/0121052 A1 | 5/2011 | Shelton, IV et al. |

* cited by examiner

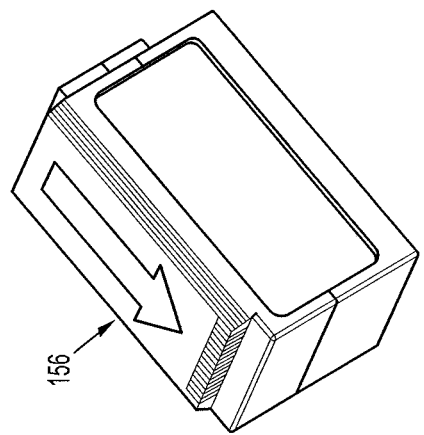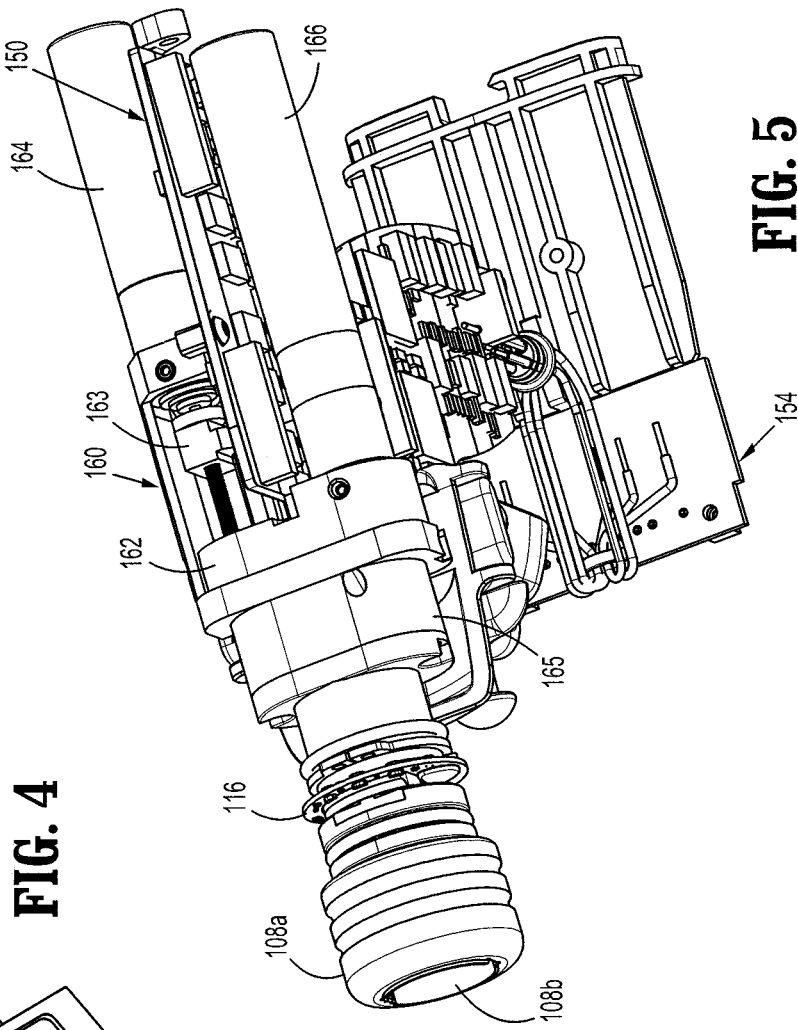

SURGICAL INSTRUMENT WITH RAPID POST EVENT DETECTION

BACKGROUND

1. Technical Field

The present disclosure relates to surgical apparatuses, devices and/or systems for performing endoscopic surgical procedures and methods of use thereof. More specifically, the present disclosure relates to electromechanical, hand-held surgical apparatus, devices and/or systems configured for use with removable disposable end effectors and/or single use end effectors for clamping, cutting and/or stapling tissue.

2. Background of the Related Art

A number of surgical device manufacturers have developed product lines with proprietary drive systems for operating and/or manipulating electromechanical surgical devices. In many instances the electromechanical surgical devices include a reusable handle assembly, and disposable or single use end effectors. The end effectors are selectively connected to the handle assembly prior to use and then disconnected from the handle assembly following use in order to be disposed of or in some instances sterilized for re-use.

Many of these electromechanical surgical devices include complex drive components that utilize a variety of user interfaces that accept user inputs (e.g., controls) for controlling the devices as well as provide feedback to the user. To prevent inadvertent activation, various lockout mechanisms exist. However, existing mechanisms only provide a single safety check.

Unlike purely mechanical systems, powered systems possess the ability to detect and react to some failures even after they have occurred. If this detection is completed in a rapid manner, corrective actions and emergency measures can be implemented to reduce and/or prevent patient and/or user harm. Accordingly, there is a need for systems and apparatuses having redundant safety mechanisms that can detect such failures.

SUMMARY

The present disclosure provides a surgical instrument including: a handle assembly; a jaw assembly including a staple cartridge containing a plurality of staples and an anvil to form the plurality of staples upon firing; a lockout mechanism configured to prevent reuse of the jaw assembly; a drive assembly at least partially located within the handle and connected to the jaw assembly and the lockout mechanism; a motor or motors operatively coupled to the drive assembly; and a controller operatively coupled to the motor, the controller configured to control supply of electrical current to the motor and to monitor a current draw of the motor, wherein the controller is further configured to terminate the supply of electrical current to the motor in response to a drop in the current draw, or detection of other triggering metrics (RPM, acceleration, etc.).

According to one aspect of the present disclosure, the jaw assembly a drive beam coupled to the lockout mechanism, the lockout mechanism configured to transition between an unlocked state and a locked state upon distal movement of the drive beam.

According to one aspect of the present disclosure, the drop in the current draw corresponds to a failure of the lockout mechanism to properly prohibit device use after the lockout mechanism should have been triggered. According to one aspect of the present disclosure, the lockout mechanism includes a locking member pivotal between an unlocked position and a locked position.

According to one aspect of the present disclosure, the jaw assembly further includes a housing defining a projection mounted therein configured to engage the locking member upon retraction of the drive beam.

The present disclosure also provides for a surgical instrument, including: a handle assembly; a disposable end effector removably coupled to the handle assembly, the disposable end effector including a jaw assembly including a staple cartridge containing a plurality of staples and an anvil to form the plurality of staples upon firing; and a drive assembly at least partially located within the handle and connected to the jaw assembly, the drive assembly including a lockout mechanism. The surgical instrument also includes a motor(s) operatively coupled to the drive assembly; a drive circuit coupled to the motor(s) and configured to measure a current draw of the motor (+ other metrics); and a controller operatively coupled to the motor, the controller configured to terminate the supply of electrical current to the motor in response to a drop in the current draw indicative of a failure of the lockout mechanism.

According to one aspect of the present disclosure, the controller is further configured to store a fault state in a memory in response to the drop in the current draw.

According to one aspect of the present disclosure, the fault state is cleared after the disposable end effector is removed from the handle assembly.

According to one aspect of the present disclosure, the controller is configured to detect the drop in the current draw based on a rate of change of the current draw.

According to one aspect of the present disclosure, the jaw assembly includes a drive beam coupled to the lockout mechanism.

According to one aspect of the present disclosure, the lockout mechanism configured to transition between an unlocked state and a locked state upon distal movement of the drive beam.

According to one aspect of the present disclosure, the drop in the current draw corresponds to a failure of the lockout mechanism to transition into the locked state upon retraction of the drive beam.

According to one aspect of the present disclosure, the lockout mechanism includes a locking member pivotal between an unlocked position and a locked position.

According to one aspect of the present disclosure, the jaw assembly further includes a housing defining a projection mounted therein configured to engage the locking member upon retraction of the drive beam.

According to one aspect of the present disclosure, the surgical instrument further includes a control assembly coupled to the controller, wherein the controller disregards user inputs in response to the drop in the current draw.

A method for controlling a surgical instrument is also provided by the present disclosure. The method including the steps of: activating a motor operatively coupled to disposable end effector. The end effector including: a drive beam coupled to a jaw assembly including a staple cartridge containing a plurality of staples and an anvil to form the plurality of staples upon firing; and a lockout mechanism coupled to the drive beam and configured to transition from an unlocked state to a locked state upon retraction of the drive beam. The method further including: measuring a current draw of the motor; and terminating supply of electric current to the motor in response to a drop off of the current draw indicative of a failure of the lockout mechanism.

According to one aspect of the present disclosure, the method further includes the step of storing a fault state in a memory in response to the drop in the current draw.

According to one aspect of the present disclosure, the method further includes the step of clearing the fault state after the disposable end effector is removed from the handle assembly.

DESCRIPTION OF THE DRAWINGS

Embodiments of the present disclosure are described herein with reference to the accompanying drawings, wherein:

FIG. 4 is a perspective view of a battery of the surgical instrument of FIG. 1, according to the present disclosure;

FIG. 5 is a top, partially-disassembled view of the surgical instrument of FIG. 1, according to the present disclosure;

DETAILED DESCRIPTION

A surgical system, in accordance with an embodiment of the present disclosure, is generally designated as 10, and is in the form of a powered hand held electromechanical instrument configured for selective attachment thereto of a plurality of different end effectors that are each configured for actuation and manipulation by the powered hand held electromechanical surgical instrument.

Figure 1:
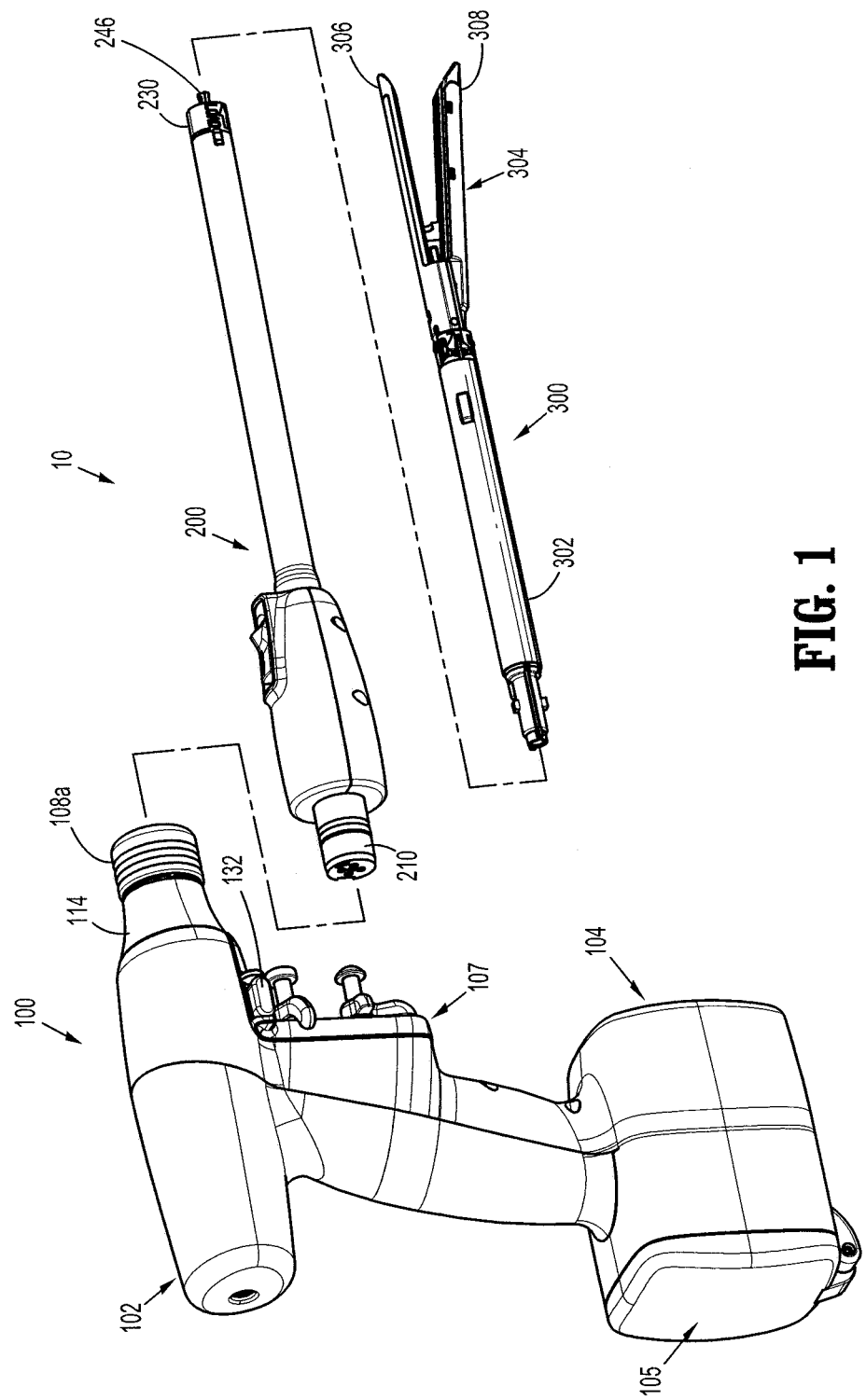
FIG. 1 is a perspective, disassembled view of an electro-mechanical surgical system including a surgical instrument, an adapter, and an end effector, according to the present disclosure.

As illustrated in FIG. 1, surgical instrument 100 is configured for selective connection with an adapter 200, and, in turn, adapter 200 is configured for selective connection with an end effector or single use loading unit or reload 300.

Figure 2:
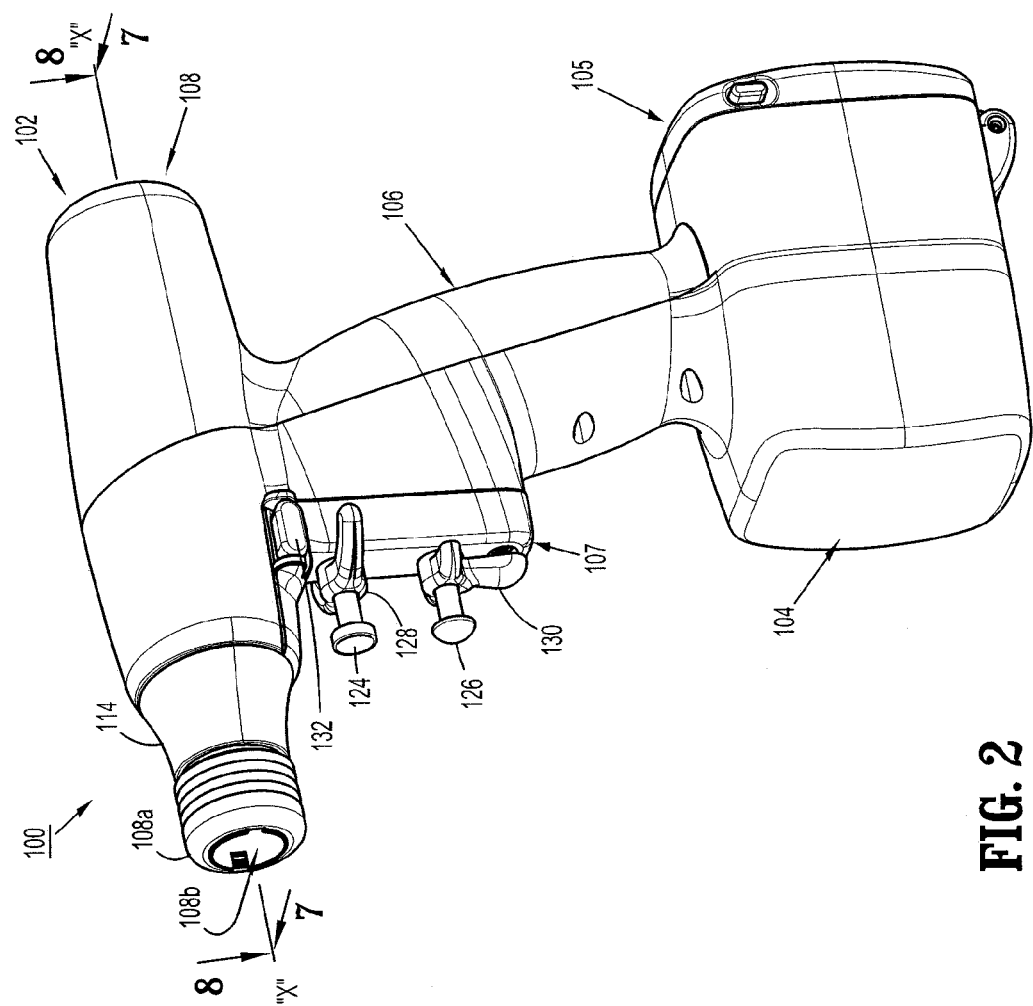
FIG. 2 is a perspective view of the surgical instrument of FIG. 1, according to the present disclosure.
Figure 3:
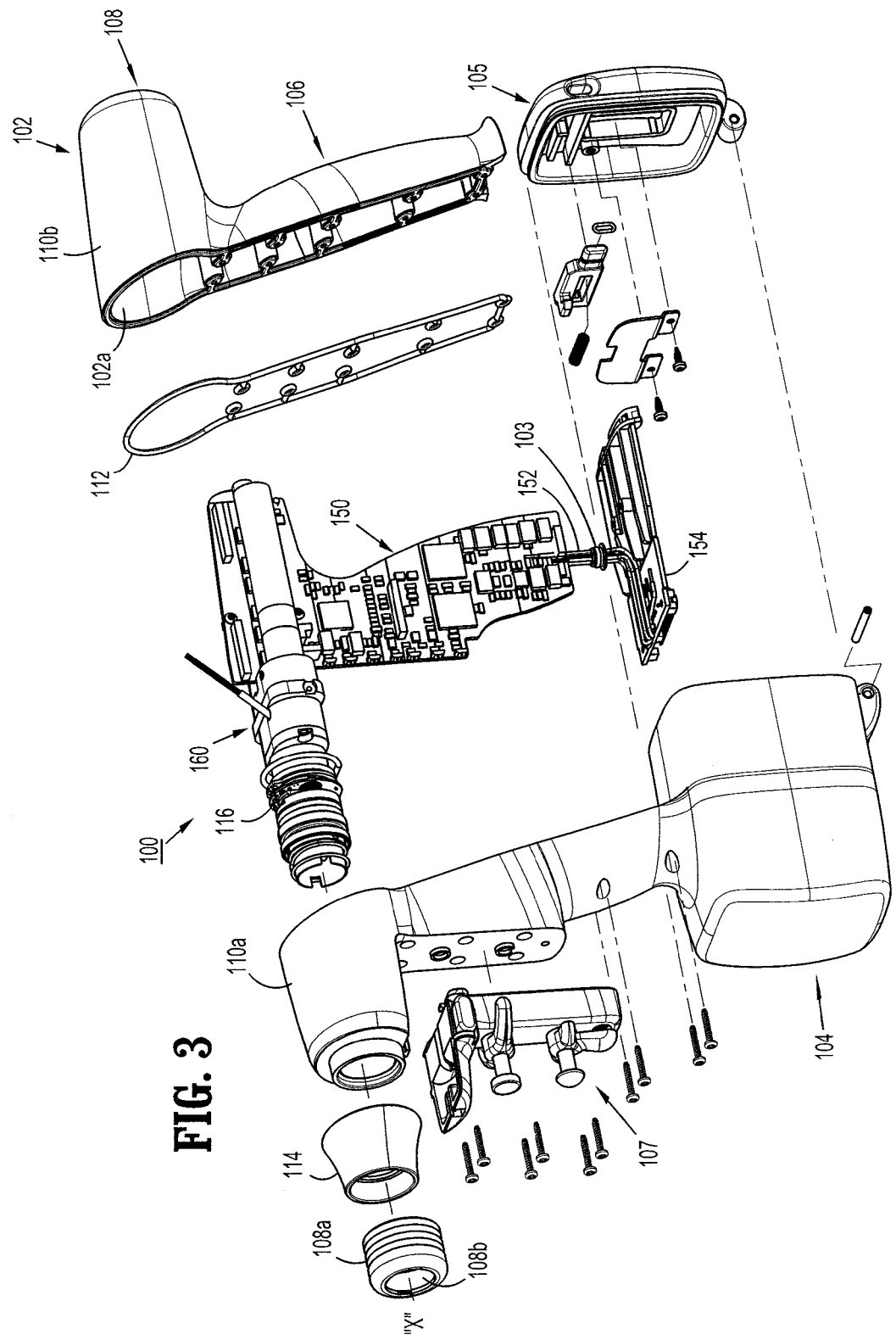
FIG. 3 is perspective, exploded view of the surgical instrument of FIG. 1, according to the present disclosure.

As illustrated in FIGS. 1-3, surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIGS. 2 and 3. Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Lower housing portion 104 of surgical instrument 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is may be a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 (see FIGS. 1 and 9) relative to proximal body portion 302 of end effector 300, to rotate end effector 300 about a longitudinal axis "X" (see FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
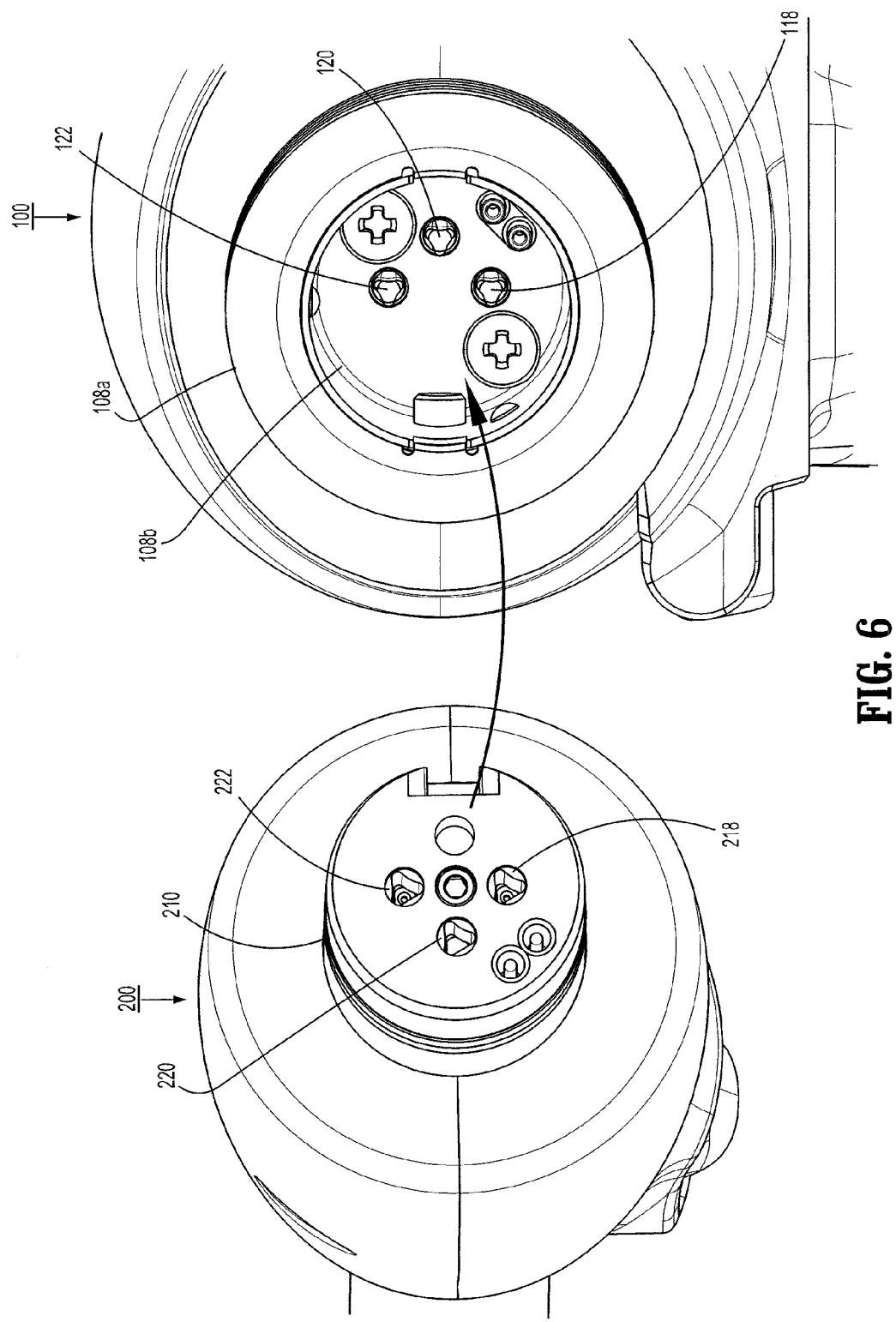
FIG. 6 is a front, perspective view of the surgical instrument of FIG. 1 with the adapter separated therefrom, according to the present disclosure.
Figure 7:
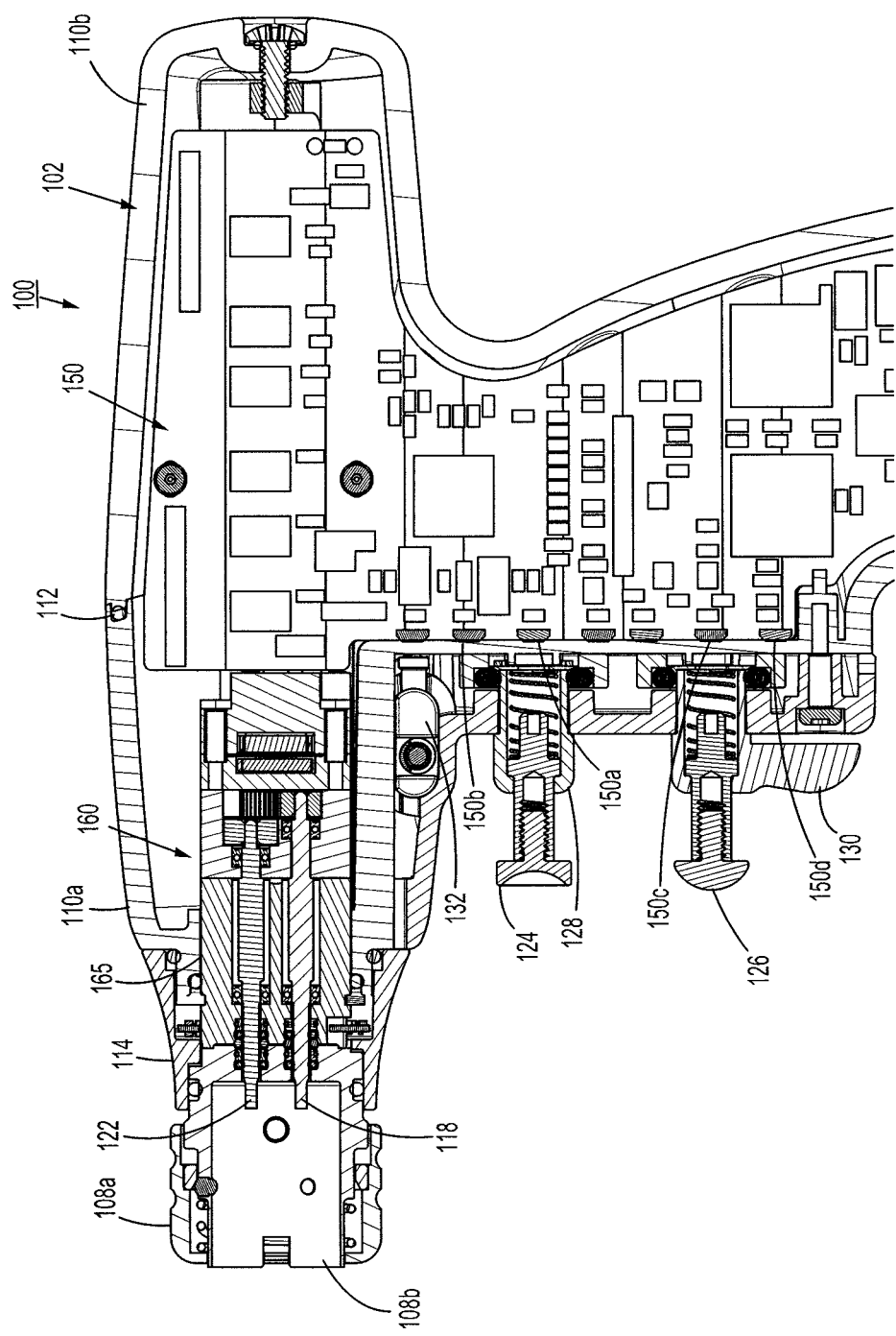
FIG. 7 is a side, cross-sectional view of the surgical instrument of FIG. 1, as taken through 7-7 of FIG. 2, according to the present disclosure.
Figure 8:
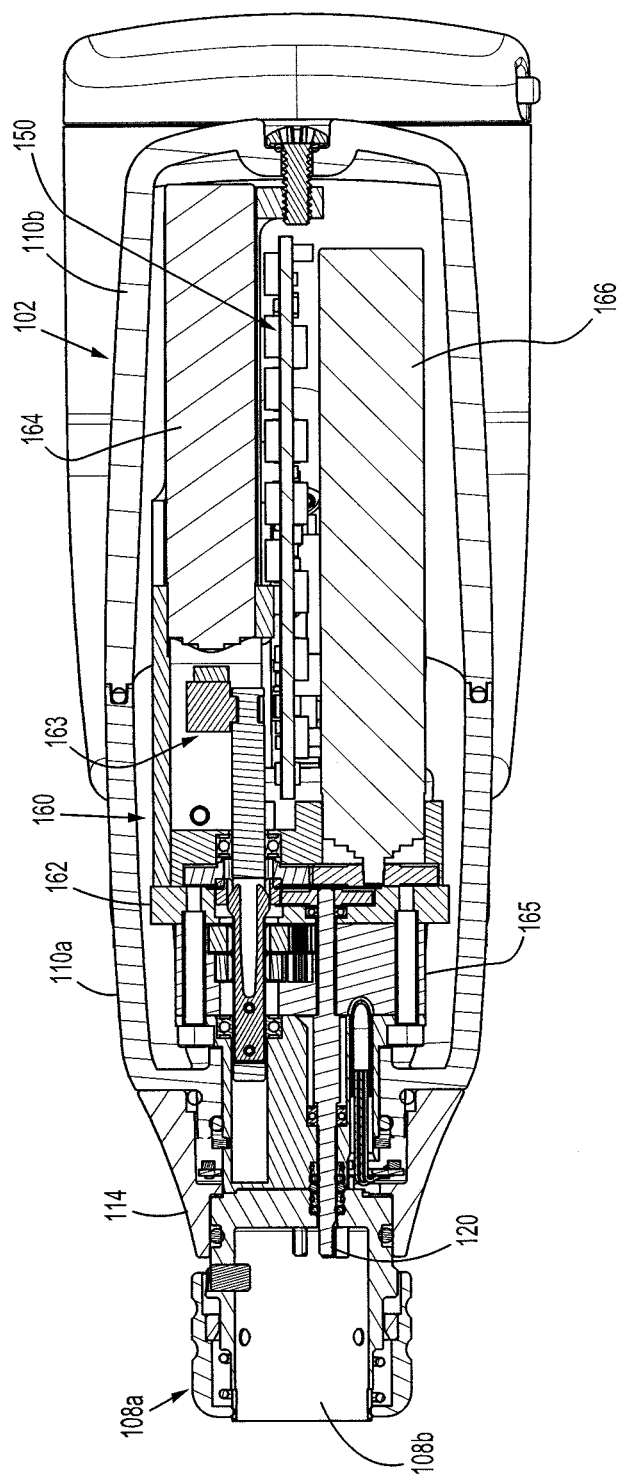
FIG. 8 is a top, cross-sectional view of the surgical instrument of FIG. 1, as taken through 8-8 of FIG. 2, according to the present disclosure.

As illustrated in FIGS. 6-8, connecting portion 108a of surgical instrument 100 has a cylindrical recess 108b that receives a drive coupling assembly 210 of adapter 200 when adapter 200 is mated to surgical instrument 100. Connecting portion 108a houses three rotatable drive connectors 118, 120, 122.

When adapter 200 is mated to surgical instrument 100, each of rotatable drive connectors 118, 120, 122 of surgical instrument 100 couples with a corresponding rotatable connector sleeve 218, 220, 222 of adapter 200 as shown in FIG. 6. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter 200.

The mating of drive connectors 118, 120, 122 of surgical instrument 100 with connector sleeves 218, 220, 222 of adapter 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160.

Since each of drive connectors 118, 120, 122 of surgical instrument 100 has a keyed and/or substantially non-rotatable interface with respective connector sleeves 218, 220, 222 of adapter 200, when adapter 200 is coupled to surgical instrument 100, rotational force(s) are selectively transferred from drive mechanism 160 of surgical instrument 100 to adapter 200.

The selective rotation of drive connector(s) 118, 120 and/or 122 of surgical instrument 100 allows surgical instrument 100 to selectively actuate different functions of end effector 300. As will be discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 transverse to longitudinal axis "X" (see FIG. 2). Additionally, the selective and independent rotation of third drive connector 122 of surgical instrument 100 corresponds to the selective and independent rotation of end effector 300 about longitudinal axis "X" (see FIG. 2) relative to handle housing 102 of surgical instrument 100.

As mentioned above and as illustrated in FIGS. 5 and 8, drive mechanism 160 includes a selector gearbox assembly 162; and a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical instrument 100 at a given time.

As illustrated in FIGS. 1-3, handle housing 102 supports a control assembly 107 on a distal surface or side of intermediate housing portion 108. The control assembly 107 is a fully-functional mechanical subassembly that can be assembled and tested separately from the rest of the instrument 100 prior to coupling thereto.

Control assembly 107, in cooperation with intermediate housing portion 108, supports a pair of finger-actuated control buttons 124, 126 and a pair rocker devices 128, 130 within a housing 107a. The control buttons 124, 126 are coupled to extension shafts 125, 127 respectively. In particular, control assembly 107 defines an upper aperture 124a for slidably receiving the extension shaft 125, and a lower aperture 126a for slidably receiving the extension shaft 127.

The control assembly 107 and its components (e.g., control buttons 124, 126 and rocker devices 128, 130) my be formed from low friction, self-lubricating, lubricious plastics or materials or coatings covering the moving components to reduce actuation forces, key component wear, elimination of galling, smooth consistent actuation, improved component and assembly reliability and reduced clearances for a tighter fit and feel consistency. This includes the use of plastic materials in the bushings, rocker journals, plunger bushings, spring pockets, retaining rings and slider components as described in further detail below. Molding the components in plastic also provides net-shape or mesh-shaped components with all of these performance attributes. Plastic components eliminate corrosion and bi-metal anodic reactions under electrolytic conditions such as autoclaving, steam sterilizations and cleaning. Press fits with lubricious plastics and materials also eliminate clearances with minimal strain or functional penalties on the components when compared to similar metal components.

Suitable materials for forming the components of the control assembly 107 include, but are not limited to, polyamines, polyphenylene sulfides, polyphthalamides, polyphenylsulfones, polyether ketones, polytetrafluoroethylenes, and combinations thereof. These components may be used in the presence or absence of lubricants and may also include additives for reduced wear and frictional forces.

Reference may be made to a commonly-owned U.S. patent application Ser. No. 13/331,047, the entire contents of which are incorporated by reference herein, for a detailed discussion of the construction and operation of the surgical instrument 100.

Figure 9:
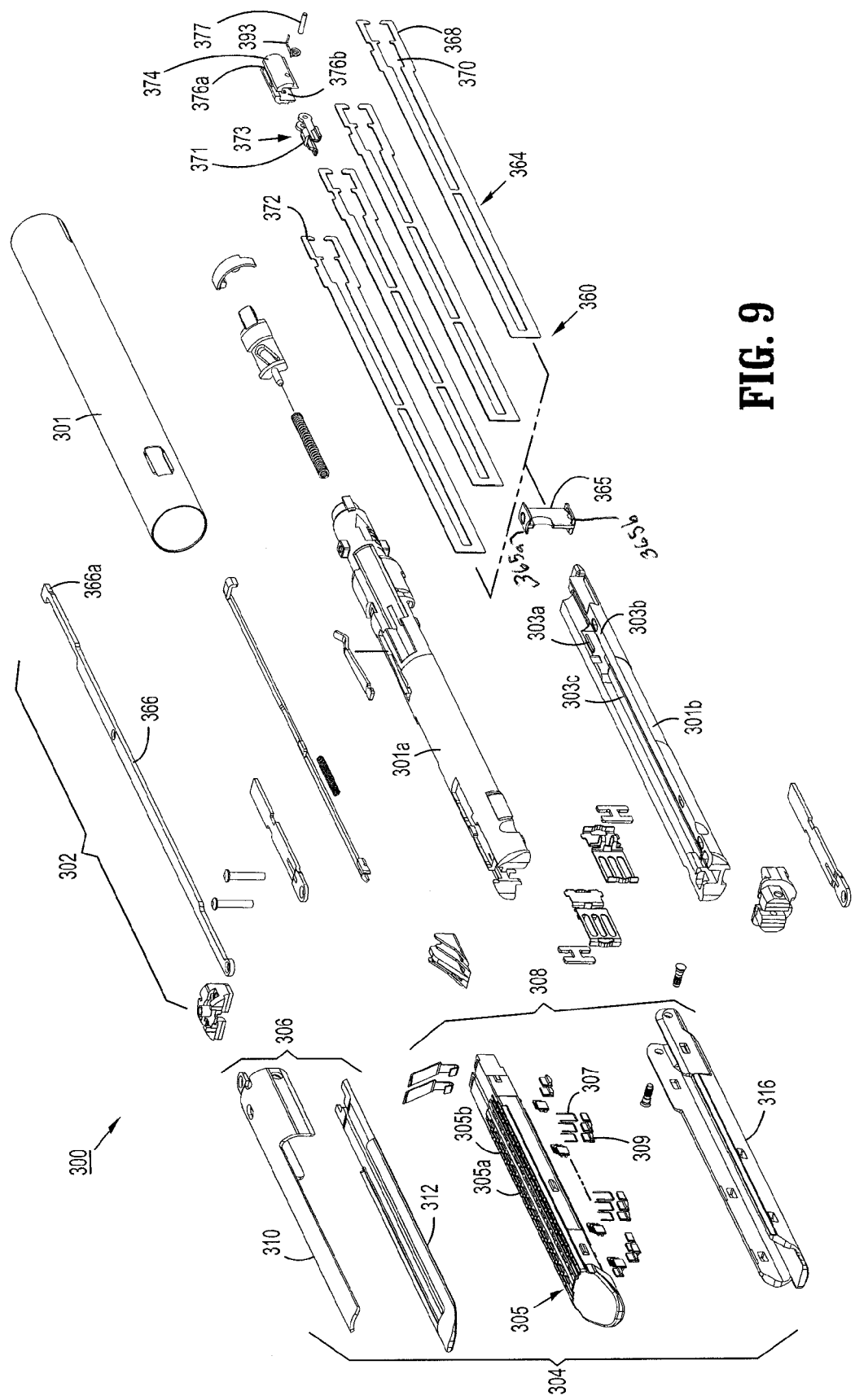
FIG. 9 is a perspective, exploded view of a end effector of FIG. 1, according to the present disclosure.

Referring to FIG. 9, drive assembly 360 of end effector 300 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376a which receives a connection member of drive tube 246 (FIG. 1) of adapter 200 when end effector 300 is attached to distal coupling 230 of adapter 200.

When drive assembly 360 is advanced distally within tool assembly 304, an upper beam 365a of clamping member 365 moves within a channel defined between anvil plate 312 and anvil cover 310 and a lower beam 365b moves over the exterior surface of carrier 316 to close tool assembly 304 and fire staples therefrom.

Proximal body portion 302 of end effector 300 includes a sheath or outer tube 301 enclosing an upper housing portion 301a and a lower housing portion 301b. The housing portions 301a and 301b enclose an articulation link 366 having a hooked proximal end 366a which extends from a proximal end of end effector 300. Hooked proximal end 366a of articulation link 366 engages a coupling hook (not shown) of adapter 200 when end effector 300 is secured to distal housing 232 of adapter 200. When drive bar 258 of adapter 200 is advanced or retracted as described above, articulation link 366 of end effector 300 is advanced or retracted within end effector 300 to pivot tool assembly 304 in relation to a distal end of proximal body portion 302.

As illustrated in FIG. 9 above, cartridge assembly 308 of tool assembly 304 includes a staple cartridge 305 supportable in carrier 316. The cartridge can be permanently installed in the end effector 300 or can be arranged so as to be removable and replaceable. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of instrument 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject staples 307 therefrom for formation against anvil plate 312.

The hollow drive member 374 includes a lockout mechanism 373 that prevents a firing of previously fired end effectors 300. The lockout mechanism 373 includes a locking member 371 pivotally coupled within a distal porthole 376b via a pin 377, such that locking member 371 is pivotal about pin 377 relative to drive member 374.

Figure 10B:
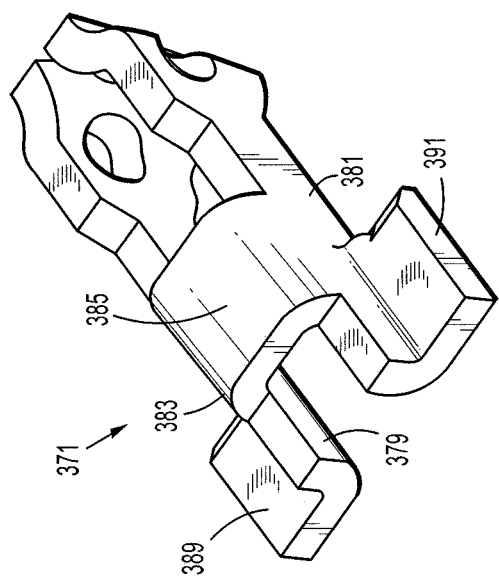
FIG. 10B is a perspective view of the locking member of FIG. 10A according to the present disclosure.
Figure 10A:
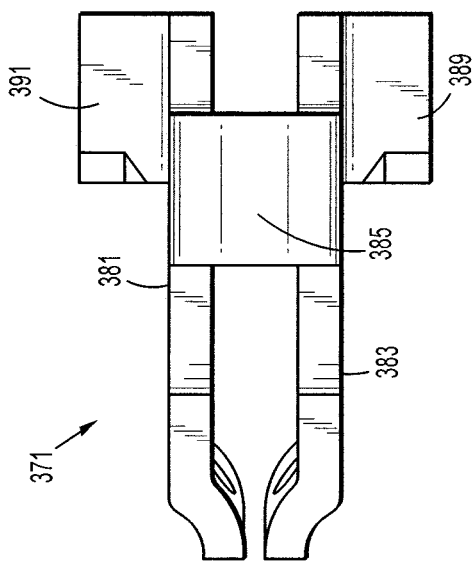
FIG. 10A is a top view of a locking member according to the present disclosure.

With reference to FIGS. 10A and 10B, locking member 371 defines a channel 379 formed between elongate glides 381 and 383. Web 385 joins a portion of the upper surfaces of glides 381 and 383. Web 385 is configured and dimensioned to fit within the porthole 376b of the drive member 374. Horizontal ledges 389 and 391 extend from glides 381 and 383 respectively. As best shown in FIG. 9, a spring 393 is disposed within the drive member 374 and engages horizontal ledge 389 and/or horizontal ledge 391 to bias locking member 371 downward.

In operation, the locking member 371 is initially disposed in its pre-fired position at the proximal end of the housing portions 301a and 301b with horizontal ledge 389 and 391 resting on top of projections 303a, 303b formed in the sidewalls of housing portion 301b. In this position, locking member 371 is held up and out of alignment with a projection 303c formed in the bottom surface of housing portion 301b, distal of the projection 303a, 303b, and web 385 is in longitudinal juxtaposition with shoulder 370 defined in drive beam 364. This configuration permits the anvil 306 to be opened and repositioned onto the tissue to be stapled until the surgeon is satisfied with the position without activating locking member 371 to disable the disposable end effector 300.

Upon distal movement of the drive beam 364 by the drive tube 246, locking member 371 rides off of projections 303a, 303b and is biased into engagement with housing portion 301b by the spring 393, distal of projection 303c. Locking member 371 remains in this configuration throughout firing of the apparatus.

Upon retraction of the drive beam 364, after at least a partial firing, locking member 371 passes under projections 303a, 303b and rides over projection 303c of housing portion 301b until the distal-most portion of locking member 371 is proximal to projection 303c. The spring 393 biases locking member 371 into juxtaposed alignment with projection 303c, effectively disabling the disposable end effector. If an attempt is made to reactuate the apparatus, loaded with the existing end effector 300, the locking member 371 will abut projection 303c of housing portion 301b and will inhibit distal movement of the drive beam 364.

The end effector 300 may also include one or more mechanical lockout mechanisms, such as those described in commonly-owned U.S. Pat. Nos. 5,071,052, 5,397,046, 5,413,267, 5,415,335, 5,715,988, 5,718,359, 6,109,500, the entire contents of all of which are incorporated by reference herein.

Figure 11:
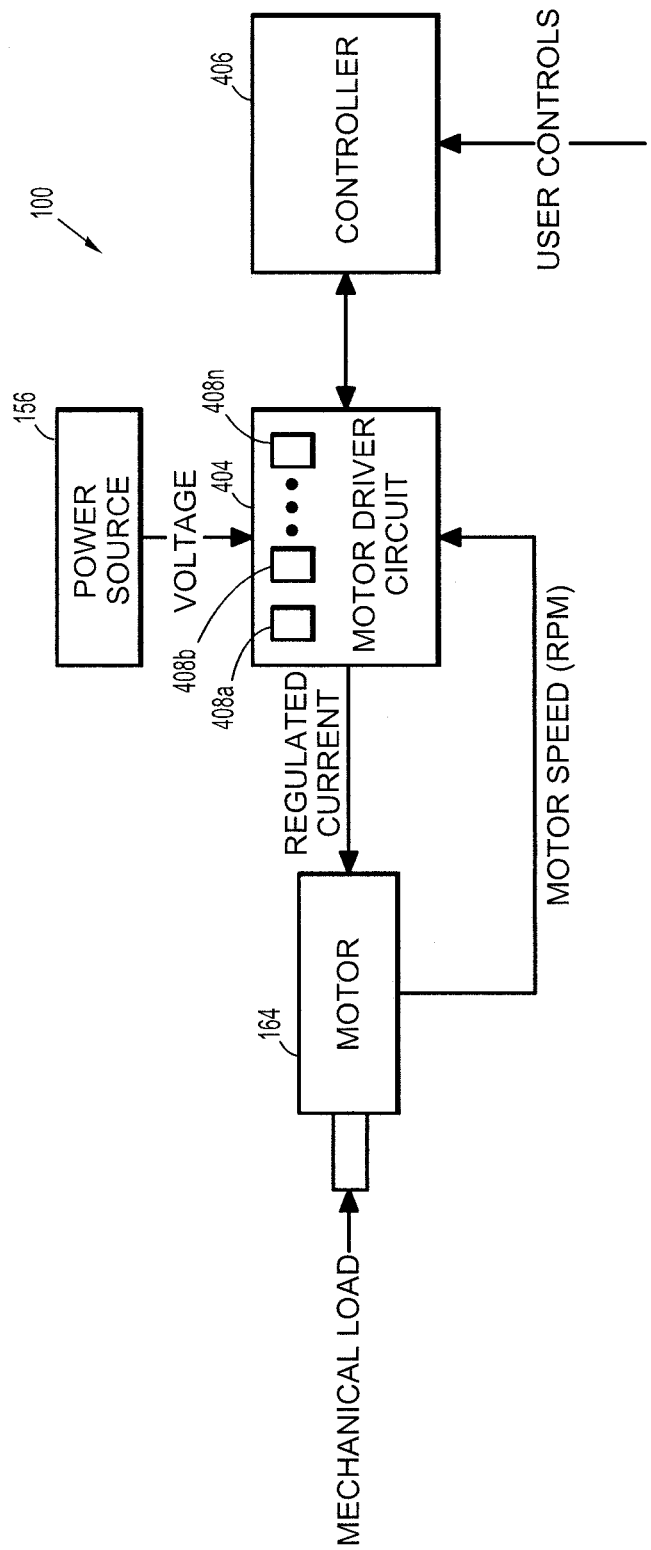
FIG. 11 is a schematic diagram of the surgical instrument of FIG. 1 according to the present disclosure.

Another embodiment of the instrument 100 is shown in FIG. 11. The instrument 100 includes the motor 164. The motor 164 may be any electrical motor configured to actuate one or more drives (e.g., rotatable drive connectors 118, 120, 122 of FIG. 6). The motor 164 is coupled to the battery 156, which may be a DC battery (e.g., rechargeable lead-based, nickel-based, lithium-ion based, battery etc.), an AC/DC transformer, or any other power source suitable for providing electrical energy to the motor 164.

The battery 156 and the motor 164 are coupled to a motor driver circuit 404 disposed on the circuit board 154 which controls the operation of the motor 164 including the flow of electrical energy from the battery 156 to the motor 164. The driver circuit 404 includes a plurality of sensors 408a, 408b, ... 408n configured to measure operational states of the motor 164 and the battery 156. The sensors 408a-n may include voltage sensors, current sensors, temperature sensors, pressure sensors, telemetry sensors, optical sensors, and combinations thereof. The sensors 408a-408n may measure voltage, current, and other electrical properties of the electrical energy supplied by the battery 156. The sensors 408a-408n may also measure rotational speed as revolutions per minute (RPM), torque, temperature, current draw, and other operational properties of the motor 164. RPM may be determined by measuring the rotation of the motor 164. Position of various drive shafts (e.g., rotatable drive connectors 118, 120, 122 of FIG. 6) may be determined by using various linear sensors disposed in or in proximity to the shafts or extrapolated from the RPM measurements. In embodiments, torque may be calculated based on the regulated current draw of the motor 164 at a constant RPM. In further embodiments, the driver circuit 404 and/or the controller 406 may measure time and process the above-described values as a function thereof, including integration and/or differentiation, e.g., to determine rate of change of the measured values and the like.

The driver circuit 404 is also coupled to a controller 406, which may be any suitable logic control circuit adapted to perform the calculations and/or operate according to a set of instructions described in further detail below. The controller 406 may include a central processing unit operably connected to a memory which may include transitory type memory (e.g., RAM) and/or non-transitory type memory (e.g., flash media, disk media, etc.). The controller 406 includes a plurality of inputs and outputs for interfacing with the driver circuit 404. In particular, the controller 406 receives measured sensor signals from the driver circuit 404 regarding operational status of the motor 164 and the battery 156 and, in turn, outputs control signals to the driver circuit 404 to control the operation of the motor 164 based on the sensor readings and specific algorithm instructions, which are discussed in more detail below. The controller 406 is also configured to accept a plurality of user inputs from a user interface (e.g., switches, buttons, touch screen, etc. of the control assembly 107 coupled to the controller 406). A removable memory card or chip may be provided, or data can be downloaded wirelessly.

The present disclosure provides for an apparatus and method for controlling the instrument 100 or any other powered surgical instrument, including, but not limited to, linear powered staplers, circular or arcuate powered staplers, graspers, electrosurgical sealing forceps, rotary tissue blending devices, and the like. In particular, torque, RPM, position, and acceleration of drive shafts of the instrument 100 can be correlated to motor characteristics (e.g., current draw). The present disclosure also provides a feedback system and method for controlling the instrument 100 based on external operating conditions such as firing difficulty encountered by the instrument 100 due to tissue thickness. In addition, the present disclosure provides for modeling of different usages of the instrument 100 in response to the external operating conditions (e.g., specific failures) to derive internal system feedback.

The sensor information from the sensors 408a-n is used by the controller 406 to alter operating characteristics of the instrument 100 and/or notify users of specific operational conditions. In embodiments, the controller 406 controls (e.g., limits) the current supplied to the motor 164 to control the operation of the instrument 100.

Figure 12:
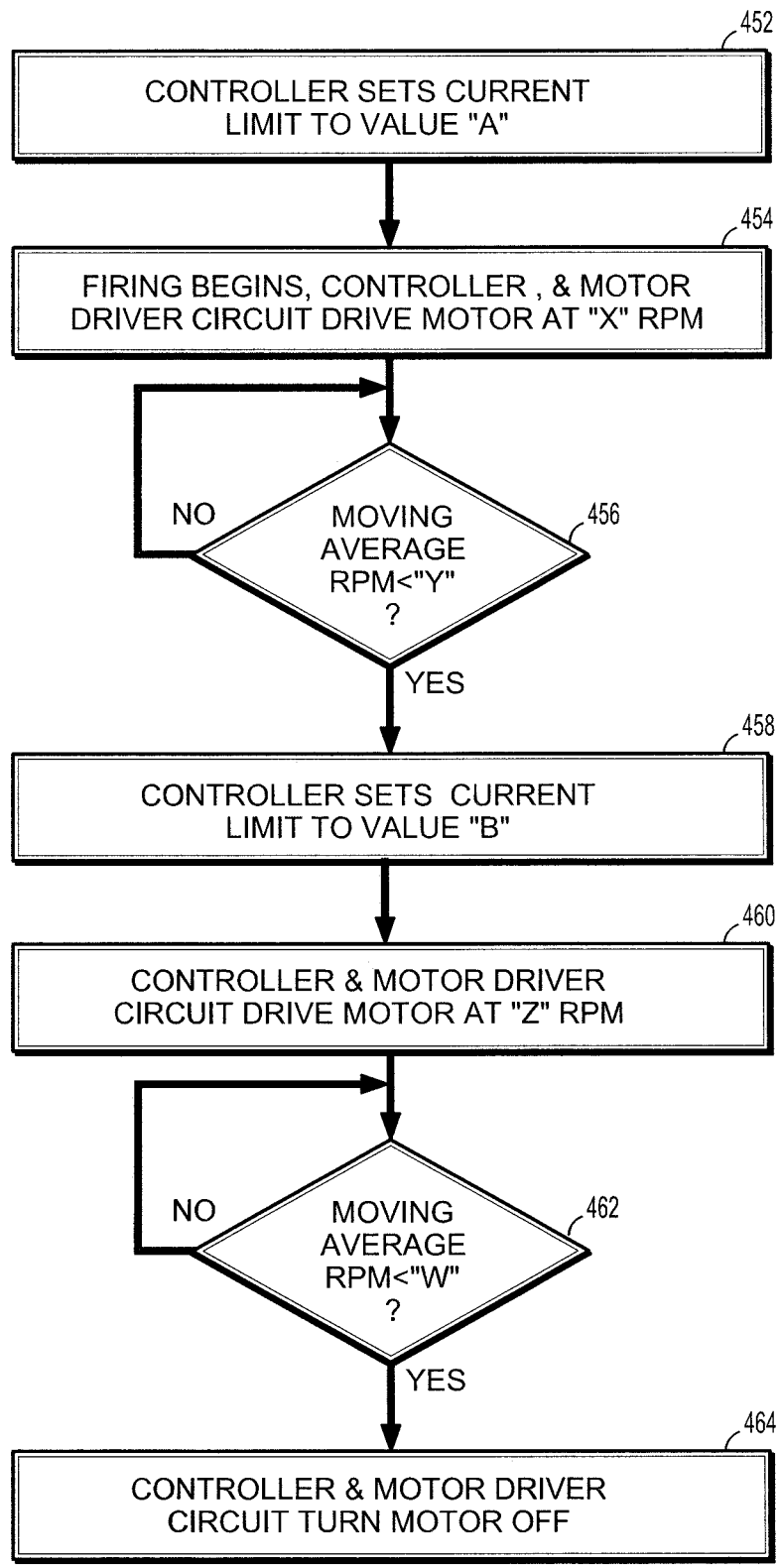
FIG. 12 is a flow chart of a method for controlling the surgical stapler of FIG. 1 according to the present disclosure.

FIG. 12 shows a method according to the present disclosure for controlling the instrument 100, and in particular, the motor 164. The method may be implemented as software instructions (e.g., algorithm) stored in the controller 406. In step 452, the controller 406 sets the current to be supplied to the motor 164 to a first current limit value "A." This may be done manually or automatically, e.g., preloaded from a look-up table stored in memory. The controller 406 also stores first upper and lower RPM limit values "X" and "Y," respectively, associated with the first current limit value "A." In step 454, the controller 406 commences operation of the instrument 100 by signaling the motor 164 to rotate the drive screw 74 to clamp tissue and/or drive staples therethrough. The controller 406 signals the drive circuit 404 to drive the motor 164 at the upper RPM limit value "X."

In step 456, the drive circuit 404 continually monitors RPM of the motor 164 and provides the measurement signals to the controller 406. The controller 406 compares the measured RPM signals to the lower RPM limit value "Y." If the value is above the lower RPM limit value "Y" then the drive circuit 404 continues to drive the motor 164 at the upper RPM limit value "X." If the value is below the lower RPM limit "Y," which denotes that the motor 164 has encountered resistance during firing, e.g., thicker tissue, an obstruction, etc., then in step 458 the controller 406 sets the current supplied to the motor 164 to a second current limit value "B."

The controller 406 also stores second upper and lower RPM limit values "Z" and "W," respectively, for the second current limit value "B." The second current limit value "B" is higher than the first current limit value "A" since higher current increases the torque and RPM of the motor 164 to overcome the resistance encountered during stapling. In step 460, the controller 406 drives the motor 164 at the upper RPM limit value "Z."

In step 462, the drive circuit 404 continually monitors RPM of the motor 164 and provides the measurement signals to the controller 406. The controller 406 compares the measured RPM signals to the lower RPM limit value "W." If the value is above the lower RPM limit value "W" then the drive circuit 404 continues to drive the motor 164 at the upper RPM limit value "Z." If the value is below the lower RPM limit value "W," which denotes that the motor 164 has encountered further resistance during firing, then in step 464 the controller 406 terminates current being supplied to the motor 164. The second current limit value "B" acts as a final current value at which the motor 164 may be operated.

In embodiments, multiple current limit values may be set for the motor 164 and the drive circuit 404 to allow the controller 406 to switch between multiple current limit values based on the encountered resistances. Each of the current limit values may also be associated with corresponding upper and lower RPM limit values at which the controller 406 switches to a neighboring current limit value. In further embodiments, the method may switch back to a lower current limit value if the encountered resistance has lowered, which may be detected based on a lower current draw and/or higher RPM limit values.

Figure 13:
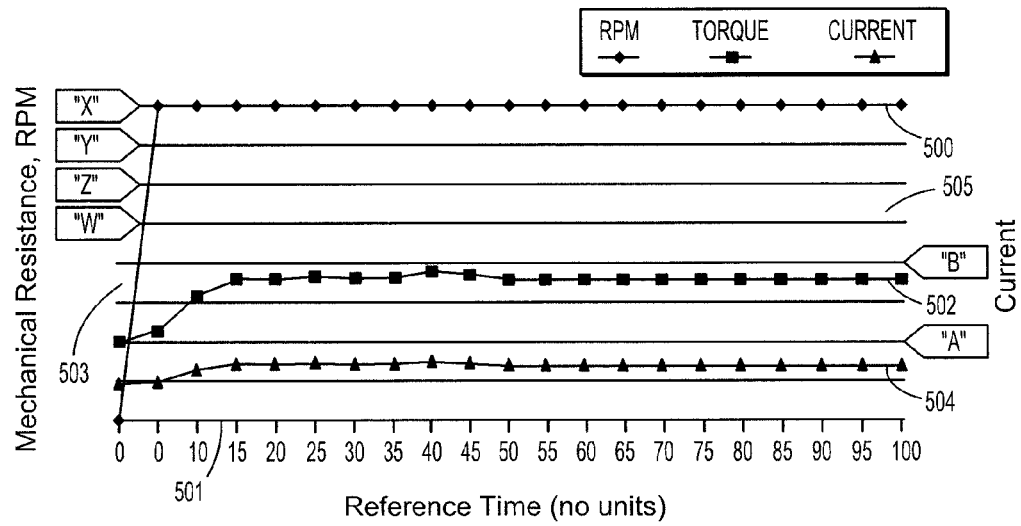
FIGS. 13-15 are plots of mechanical resistance, rotational speed, and current applied to a motor of the surgical stapler as controlled by the method of the present disclosure.
Figure 14:
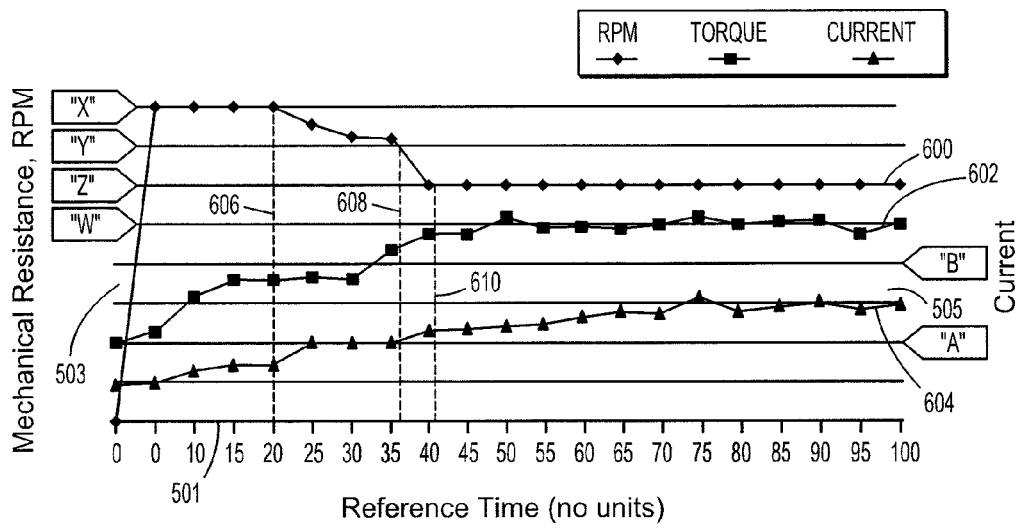
Figure 15:
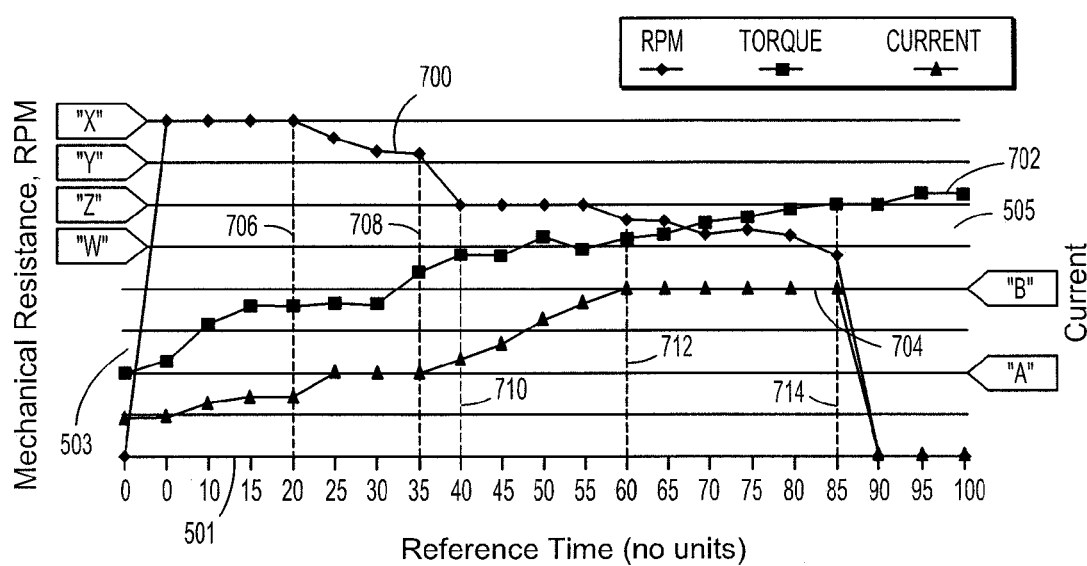

FIGS. 13-15 illustrate performance plots of the motor 164 during various operational situations. FIGS. 13-15 show plots of rotational speed, torque, and current as a function of time. In FIGS. 13-15, horizontal axis 501 represents reference time expressed as a unitless scale, left vertical axis 503 represents mechanical resistance on the motor 164 (e.g., torque) and RPM of the motor 164, which are not proportional, and right vertical axis 505 represents the current supplied to the motor 164. The left vertical axis 503 includes first upper and lower RPM limit values "X" and "Y," respectively, and second upper and lower RPM limit values "Z" and "W." The right vertical axis 505 includes first and second current limit values "A" and "B."

FIGS. 13-15 illustrate various embodiments of the method of FIG. 12. FIG. 13 shows an RPM plot 500, a torque plot 502, and a current plot 504. As the firing process commences, the mechanical load on the motor 164 remains low and the RPM of the motor 164 are held constant at the first upper RPM limit value "X" as shown by the plot 500. The method does not progress beyond the step 456 since the RPMs did not drop below the lower RPM limit value "Y." Consequently, the first current limit value "A" is not reached during the firing process as represented by the plot 504 and the torque is also held constant as shown by the plot 502.

FIG. 14 shows an RPM plot 600, a torque plot 602, and a current plot 604. As the firing process commences, the mechanical load is initially constant as illustrated in FIG. 13 but increased strain on the motor 164 is illustrated at a point

606 of FIG. 14. As the load is increasing, the motor 164 requires more current to maintain the RPM at the upper RPM limit value "X." The controller 406 signals the drive circuit 404 to limit the current below the current limit value "A."

Increase in the mechanical load results in the RPMs of the motor 164 dropping below the lower RPM limit value "Y" and the current exceeding the first current limit value "A" at a point 608 as represented by the plot 600. With reference to the flow chart of FIG. 12, at step 456 of the method, the drop in RPMs of the motor 164 is detected and the higher current limit value "B" along with upper and lower RPM limit values "Z" and "W" are set in steps 458 and 460, as described above. At a point 610, once the higher current limit value "B" is set, the motor 164 continues its operation at the upper RPM limit value "Z" until the firing process is complete.

FIG. 15 illustrates an RPM plot 700, a torque plot 702, and a current plot 704. As the firing process commences, the mechanical load is initially constant as illustrated in FIGS. 13 and 14 but increased strain on the motor 164 is illustrated at a point 706. As the load is increasing, the motor 164 requires more current to maintain the RPM at the upper RPM limit value "X." The controller 406 signals the drive circuit 404 to limit the current below the current limit value "A."

Increase in the mechanical load results in the RPMs of the motor 164 dropping below the lower RPM limit value "Y" at a point 708 as represented by the plot 700. With reference to the flow chart of FIG. 12, at step 456 of the method, the drop in RPMs of the motor 164 is detected and the higher current limit value "B" along with upper and lower RPM limit values "Z" and "W" are set in steps 458 and 460, as described above.

At a point 710, once the higher current limit value "B" is set, the motor 164 continues its operation at the upper RPM limit value "Z" in response to the higher mechanical load until a point 712, at which the motor 164 encounters additional resistance or strain. As the load is increasing, the motor 164 requires more current to maintain the RPM at the upper RPM limit value "Z." The controller 406 signals the drive circuit 404 to limit the current below the current limit value "B."

Further increase in the mechanical load results in the RPMs of the motor 164 dropping below the lower RPM limit value "W" and the current exceeding the second current limit value "B" at a point 712 as represented by the plot 700. With reference to the flow chart of FIG. 12, at step 462 of the method, the second drop in RPMs of the motor 164 is detected and the controller 406 signals the driver circuit 404 to shut off the motor 164 at a point 714, as seen in FIG. 15.

The present disclosure provides several advantages to device performance, safety, and to the end users experience. The instrument 100 provides an intuitive feedback method to users during operation including visual and audible feedback. In particular, the present disclosure lowers the RPM of the motor 164 or shuts the motor 164 as the instrument 100 encounters increased mechanical load. This basic performance feedback fulfills a larger user need which was unaddressed by conventional powered devices. Its implementation allows users to more effectively use powered instruments.

In any of the embodiments disclosed herein, the reload 300 and adapter 200 can be used with an instrument 100 that is powered by air pressure, alternating current (such as a wall socket), a generator, or other means. In any of the embodiments, the instrument 100 and adapter 200 can utilize two drive shafts rather than three, or more than three shafts.

In any of the embodiments disclosed herein, the controller can store information about the current, RPM, forces, time, pressure, or other data concerning the use of the system. In any of the embodiments, sensors can be provided in the reload 300, or other places in the system. In any of the embodiments disclosed herein, the memory can wirelessly transfer the data, upon command or automatically, to another storage device, or a removable chip or card can be provided to store such data.

Use of this algorithm to selectively and intelligently alter operational speeds can offer further benefits. In embodiments, the instrument 100 may decrease firing speed under excessive conditions. This slowing causes firings to take longer to complete. As a result additional time is provided in which tissues can compress and fluids can disperse. This allows reloads to be fired successfully onto a larger tissue masses than would be possible with a static firing speed stapler. Specific changes to RPM and current limit values in specific situations can reduce device fatigue, improve staple formation, lower internal temperatures, eliminate the need for duty cycles, increase devices functional lifetime, and reliability.

During the use of any surgical instruments one or more safety mechanisms, such as the lockout mechanism 373, may fail. The controller 404 determines firing progress of the end effector 300 based on distance traveled by rotatable drive connectors 118, 120, 122 of FIG. 6. Completion and/or failure of the firing status is stored in the memory and may be annunciated to the user using various status indicators (e.g., LEDs). Although specific failure of the lockout mechanism 373 is described herein, it is envisioned that correlation of the metrics of the motor 164 may be used to provide an additional safety check of the mechanical safety lockouts.

Figure 16:
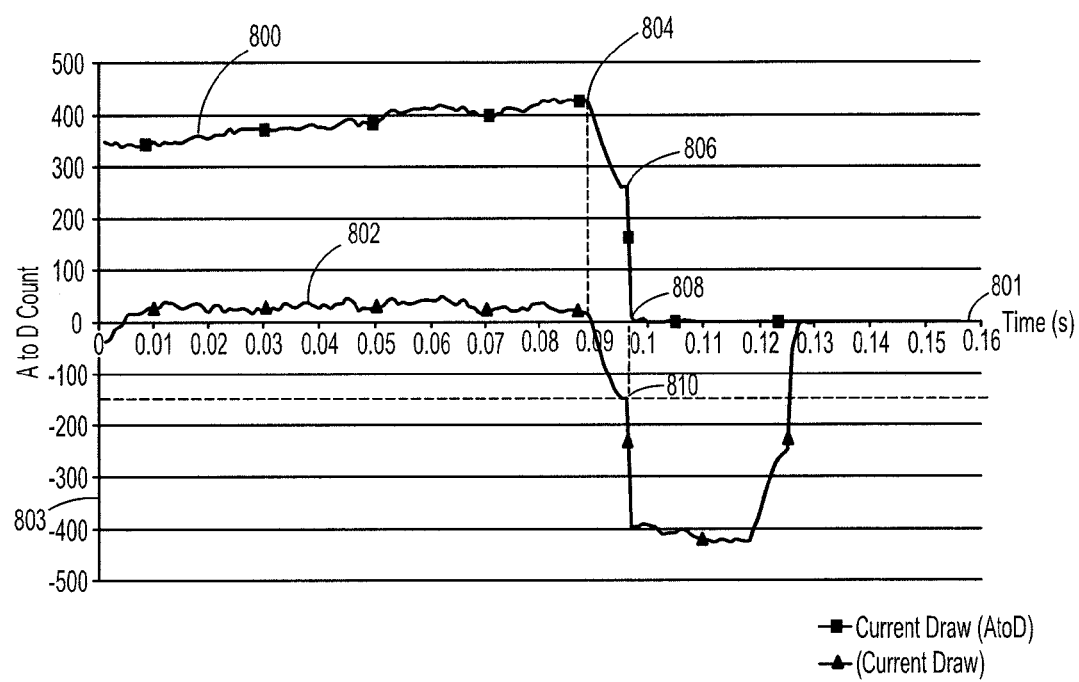
FIG. 16 is a plot of current draw of the motor of the surgical stapler as controlled by the method of the present disclosure.

FIG. 16 illustrates a performance plot of the motor 164 during mechanical failure of the lockout mechanism of the 373. In FIG. 16, horizontal axis 801 represents reference time expressed in seconds, left vertical axis 803 represents current draw of the motor 164. FIG. 16 also shows a current draw plot 800 and a processed current draw plot 802. As the firing process commences, the mechanical load on the motor 164 slightly increases as the drive beam 364 is advanced as shown by the plot 800 until a point 804. The current draw then drops off precipitously until a point 806, which is indicative of the failure of the lockout mechanism 373 (e.g., the locking member 371 fails to engage the protrusion 303c). Supply of current is completely shut off at a point 808 as illustrated by an almost instantaneous drop of current to 0 amperes (A).

The plot 802 shows a processed plot that is indicative of the current draw. In particular, the current draw of the plot 800 may be processed by the driver circuit 404 and/or the controller 406 to output the plot 802. Plot 802 may be generated as a function of the current draw by the motor 164 (e.g., plot 800) and one or more additional metrics of the motor 164 including, but not limited to, time, rotational speed, torque, temperature, position of various drive shafts, and combinations thereof.

The plot 802 tracks the initial current draw until the point 804. The first drop between points 804 and 806 is also reflected in the processed plot 802, which is indicative of the failure of the lockout mechanism 373. The current draw then drops off precipitously until the point 808. Supply of current is also completely shut off at the point 808 as illustrated by an almost instantaneous drop in the plot 802 at a point 810.

The driver circuit 404 and/or the controller 406 may detect the drop off of the current draw by monitoring the rate of change of the current draw. In response to the detection of the failure of the lockout mechanism 373, the driver circuit 404 and/or the controller 406 stop application of current to the motor 164, thereby terminating the firing process. In addition, the driver circuit 404 and/or the controller 406 may lockout operation of the instrument 100 until end effector 300 is removed. During lockout, the instrument 100 may become completely or partially unresponsive to user inputs (e.g., actuation of the control assembly 107) and may annunciate the fault condition to the user via various status indicators (e.g., LEDs). In embodiments, the driver circuit 404 and/or the controller 406 may store in memory a fault indicator. The fault indicator may be resident in memory until the fault is cleared (e.g., by replacing the end effector 300), thus preventing reuse of the end effector 300.

The disclosed combination of the lockout mechanism 373 and the driver circuit 404 and/or the controller 406, which detect failure of the lockout mechanism 373 allows for prevention of reuse of the end effector 300. Failure of the lockout mechanism 373 (e.g., due to intentional tampering) may allow for unauthorized reloading of the previously used end effector 300. The current drop off monitoring by the driver circuit 404 and/or the controller 406 allows for prevention of reuse of the previously used end effector 300 even when the lockout mechanism 373 is absent or otherwise malfunctions. The driver circuit 404 and/or the controller 406 are configured to only trigger a fault condition when the operation of the motor 164 is indicative of a failed lockout mechanism 373. In other words, the current draw of the motor 164 does not drop off at the point 804 if the lockout mechanism 373 functions properly, thus not triggering the electronic lockout described above. In any of the embodiments disclosed herein, the surgical system can include more than one lockout in various locations, and the one or more lockouts can take various forms.

In addition to basic feedback about device performance this disclosure also provides a method for powered devices to detect and discern other external factors, e.g., thicker tissue, which previously were difficult to detect. As a result, improved cutoffs and values for limits can be implemented, greatly improving the safety of powered devices in use. Using the feedback mechanisms discussed above, users may make intelligent decisions about what settings and techniques should be used when operating the instrument 100. This intelligence can range from choosing a different reload to fire with a linear stapler, deciding to fire at a different articulation angle, to choosing to use a completely different surgical technique.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical instrument, comprising:
a handle assembly;
a jaw assembly comprising a staple cartridge containing a plurality of staples and an anvil to form the plurality of staples upon firing;
a lockout mechanism configured to prevent reuse of the jaw assembly;
a drive assembly at least partially located within the handle and connected to the jaw assembly and the lockout mechanism;
a motor operatively coupled to the drive assembly; and
a controller operatively coupled to the motor, the controller configured to control supply of electrical current to the motor and to monitor a current draw of the motor, wherein the controller is further configured to terminate the supply of electrical current to the motor in response to a drop in the current draw indicative of a failure of the lockout mechanism.

2. The surgical instrument according to claim 1, wherein the jaw assembly comprises a drive beam coupled to the lockout mechanism, the lockout mechanism configured to transition between an unlocked state and a locked state upon distal movement of the drive beam.

3. The surgical instrument according to claim 2, wherein the drop in the current draw corresponds to a failure of the lockout mechanism to transition into the locked state upon retraction of the drive beam.

4. The surgical instrument according to claim 3, wherein the lockout mechanism comprises a locking member pivotal between an unlocked position and a locked position.

5. The surgical instrument according to claim 4, wherein the jaw assembly further comprises a housing defining a projection mounted therein configured to engage the locking member upon retraction of the drive beam.

6. A surgical instrument, comprising:
a handle assembly;
a disposable end effector removably coupled to the handle assembly, the disposable end effector comprising a jaw assembly including a staple cartridge containing a plurality of staples and an anvil to form the plurality of staples upon firing;
a drive assembly at least partially located within the handle and connected to the jaw assembly, the drive assembly comprising a lockout mechanism;
a motor operatively coupled to the drive assembly;
a drive circuit coupled to the motor and configured to measure a current draw of the motor; and
a controller operatively coupled to the motor, the controller configured to terminate the supply of electrical current to the motor in response to a drop in the current draw indicative of a failure of the lockout mechanism.

7. The surgical instrument according to claim 6, wherein the controller is further configured to store a fault state in a memory in response to the drop in the current draw.

8. The surgical instrument according to claim 7, wherein the fault state is cleared after the disposable end effector is removed from the handle assembly.

9. The surgical instrument according to claim 6, wherein the controller is configured to detect the drop in the current draw based on a rate of change of the current draw.

10. The surgical instrument according to claim 6, wherein the jaw assembly comprises a drive beam coupled to the lockout mechanism.

11. The surgical instrument according to claim 10, the lockout mechanism configured to transition between an unlocked state and a locked state upon distal movement of the drive beam.

12. The surgical instrument according to claim 11, wherein the drop in the current draw corresponds to a failure of the lockout mechanism to transition into the locked state upon retraction of the drive beam.

13. The surgical instrument according to claim 12, wherein the lockout mechanism comprises a locking member pivotal between an unlocked position and a locked position.

14. The surgical instrument according to claim 13, wherein the jaw assembly further comprises a housing defining a projection mounted therein configured to engage the locking member upon retraction of the drive beam.

15. The surgical instrument according to claim 6, further comprising a control assembly coupled to the controller, wherein the controller disregards user inputs in response to the drop in the current draw.

16. A method for controlling a surgical instrument, the method comprising:
- activating a motor operatively coupled to a disposable end effector, the disposable end effector comprising:
    - a drive beam coupled to a jaw assembly comprising a staple cartridge containing a plurality of staples and an anvil to form the plurality of staples upon firing; and
    - a lockout mechanism coupled to the drive beam and configured to transition from an unlocked state to a locked state upon retraction of the drive beam;
- measuring a current draw of the motor; and
- terminating supply of electric current to the motor in response to a drop off of the current draw indicative of a failure of the lockout mechanism.

17. The method according to claim 16, further comprising: storing a fault state in a memory in response to the drop in the current draw.

18. The method according to claim 17, further comprising: clearing the fault state after the disposable end effector is removed from the handle assembly.

* * * * *